United States Patent
Wang et al.

(10) Patent No.: US 10,718,754 B2
(45) Date of Patent: Jul. 21, 2020

(54) SYSTEM AND METHOD FOR CHARACTERIZING PROTEIN DIMERIZATION

(71) Applicant: Regeneron Pharmaceuticals, Inc., Tarrytown, NY (US)

(72) Inventors: Shunhai Wang, Ossining, NY (US); Yuetian Yan, New York, NY (US)

(73) Assignee: REGENERON PHARMACEUTICALS, INC, Tarrytown, NY (US)

( * ) Notice: Subject to any disclaimer, the term of this patent is extended or adjusted under 35 U.S.C. 154(b) by 0 days.

(21) Appl. No.: 16/265,083

(22) Filed: Feb. 1, 2019

(65) Prior Publication Data

US 2019/0242877 A1   Aug. 8, 2019

Related U.S. Application Data

(60) Provisional application No. 62/625,732, filed on Feb. 2, 2018, provisional application No. 62/738,051, filed on Sep. 28, 2018.

(51) Int. Cl.
| | | |
|---|---|---|
| *A61K 39/00* | (2006.01) | |
| *G01N 33/68* | (2006.01) | |
| *A01N 1/02* | (2006.01) | |
| *A23G 9/38* | (2006.01) | |
| *A23L 3/3526* | (2006.01) | |
| *G01N 33/50* | (2006.01) | |
| *C07K 1/04* | (2006.01) | |
| *C07K 16/06* | (2006.01) | |
| *C12N 5/071* | (2010.01) | |
| *C12N 5/12* | (2006.01) | |

(52) U.S. Cl.
CPC ......... *G01N 33/5032* (2013.01); *C07K 1/047* (2013.01); *C07K 16/065* (2013.01); *C12N 5/0602* (2013.01); *C12N 5/12* (2013.01); *G01N 33/6848* (2013.01); *G01N 33/6854* (2013.01)

(58) Field of Classification Search
CPC .. A61K 2039/505; A01N 1/02; A01N 1/0221; A01N 3/00; A23B 7/055
See application file for complete search history.

(56) References Cited

U.S. PATENT DOCUMENTS

| | | |
|---|---|---|
| 6,927,004 B2 | 8/2005 | Eurlings et al. |
| 7,087,411 B2 | 8/2006 | Daly et al. |
| 7,279,159 B2 | 10/2007 | Daly et al. |
| 7,582,298 B2 | 9/2009 | Stevens et al. |
| 7,879,984 B2 | 2/2011 | Martin et al. |
| 8,043,617 B2 | 10/2011 | Stevens et al. |
| 8,062,640 B2 | 11/2011 | Sleeman et al. |
| 8,309,088 B2 | 11/2012 | Macdonald et al. |
| 8,735,095 B2 | 5/2014 | Martin et al. |
| 8,871,209 B2 | 10/2014 | Stitt et al. |
| 8,945,559 B2 | 2/2015 | Dix et al. |
| 9,018,356 B2 | 4/2015 | Sleeman et al. |
| 9,079,948 B2 | 7/2015 | Orengo et al. |
| 9,132,192 B2 | 9/2015 | Daly et al. |
| 9,173,880 B2 | 11/2015 | Dix et al. |
| 9,228,014 B2 | 1/2016 | Classon et al. |
| 9,260,515 B2 | 2/2016 | Stitt et al. |
| 9,265,827 B2 | 2/2016 | Wiegand et al. |
| 9,302,015 B2 | 4/2016 | Papadopoulos et al. |
| 9,353,176 B2 | 5/2016 | Macdonald et al. |
| 9,402,898 B2 | 8/2016 | Walsh et al. |
| 10,011,858 B2 * | 7/2018 | Igawa ................. C07K 16/18 |
| 2010/0331527 A1 | 12/2010 | Davis et al. |
| 2014/0044730 A1 | 2/2014 | Yancopoulos et al. |
| 2014/0088295 A1 | 3/2014 | Smith et al. |
| 2014/0271642 A1 | 9/2014 | Murphy et al. |
| 2014/0271653 A1 | 9/2014 | Gurnett-Bander et al. |
| 2014/0271658 A1 | 9/2014 | Murphy et al. |
| 2014/0271681 A1 | 9/2014 | Martin et al. |
| 2015/0203579 A1 | 7/2015 | Papadopoulos et al. |
| 2015/0203580 A1 | 7/2015 | Papadopoulos et al. |
| 2015/0259423 A1 | 9/2015 | Kirshner et al. |
| 2015/0266966 A1 | 9/2015 | Smith et al. |
| 2015/0313194 A1 | 11/2015 | Hu et al. |
| 2015/0337029 A1 | 11/2015 | Kyratsous et al. |
| 2015/0337045 A1 | 11/2015 | Okamoto et al. |
| 2016/0017029 A1 | 1/2016 | Walsh et al. |
| 2016/0075778 A1 | 3/2016 | Okamoto et al. |
| 2016/0215040 A1 | 7/2016 | Kyratsous et al. |

OTHER PUBLICATIONS

Wowor et al., "Analysis of SecA dimerization in solution", Biochemistry, 2014,53:3248-3260.*

Deperalta, G., et al., "Structural analysis of a therapeutic monoclonal antibody dimer by hydroxyl radical footprinting," MAbs, 5(1):86-101 (2013).

Zhang, H., et al., "Carboxyl-group footprinting maps the dimerization interface and phosphorylation-induced conformational changes of a membrane-associated tyrosine kinase," Mol Cell Proteomics, 10(6):M110.005678 (2011).

Zhang, Ying, et al., "Mapping the binding interface of VEGF and a Monoclonal Antibody Fab-1 Fragments with Fast Photochemical Oxidation of Proteins (FPOP) and Mass Spectrometry," J Am Soc Mass Spectrom, 28(5):850-858 (2017).

(Continued)

*Primary Examiner* — Barry A Chestnut
(74) *Attorney, Agent, or Firm* — Smith, Gambrell & Russell, LLP

(57) ABSTRACT

Systems and methods to characterize dimerization interfaces at the subdomain level of a protein are provided. An exemplary method includes digesting a protein dimer sample into subdomains, labeling the digested protein sample, isolating labeled dimeric and monomeric subdomain fragments, and peptide mapping the labeled sample to determine where the dimer fragments are labeled and where the dimer fragments are not labeled. Regions that show decreased labeling extents in the dimer fraction than that in the monomer fraction are likely involved or in close proximity to the dimerization interface.

22 Claims, 10 Drawing Sheets

(56) References Cited

OTHER PUBLICATIONS

The International Search Report of the International Searching Authority dated Apr. 11, 2019; 3 pages.
The Written Opinion of the International Searching Authority dated Apr. 11, 2019; 9 pages.
Ashkenazi, et al., "Protection against endotoxic shock by a tumor necrosis factor receptor immunoadhesion", Proc Natl Acad Sci USA, 88:1535, 1991.
Byrn et al., "Biological properties of a CD4 immunoadhesion", Nature 344:677, 1990.
Hollenbaugh, et al., "Construction of Immunoglobulin Fusion Proteins", Cur Prot Immun, Supl., 4, pp. 10.19.1-10.19.11, 2002.
Lawrence, "Billion dollar babies—biotech drugs as blockbusters", Nat Biotech, 25:380-2, 2007.
Walsh, "Biopharmaceutical benchmarks 2014", Nat Biotech, 32:992-1000, 2014.

\* cited by examiner

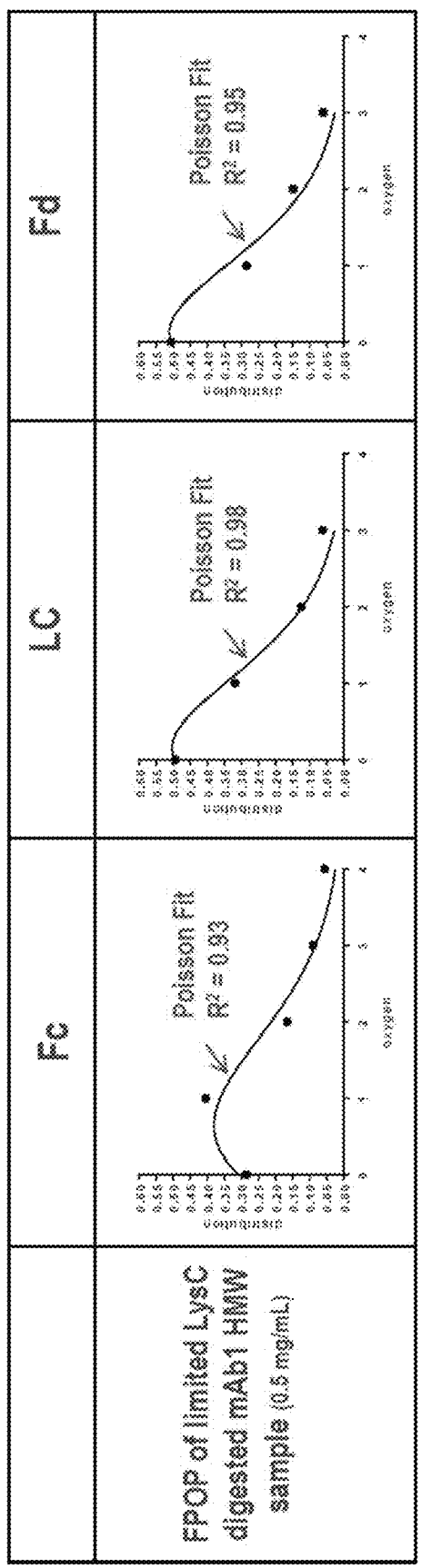
Figure 4A Figure 4B Figure 4C

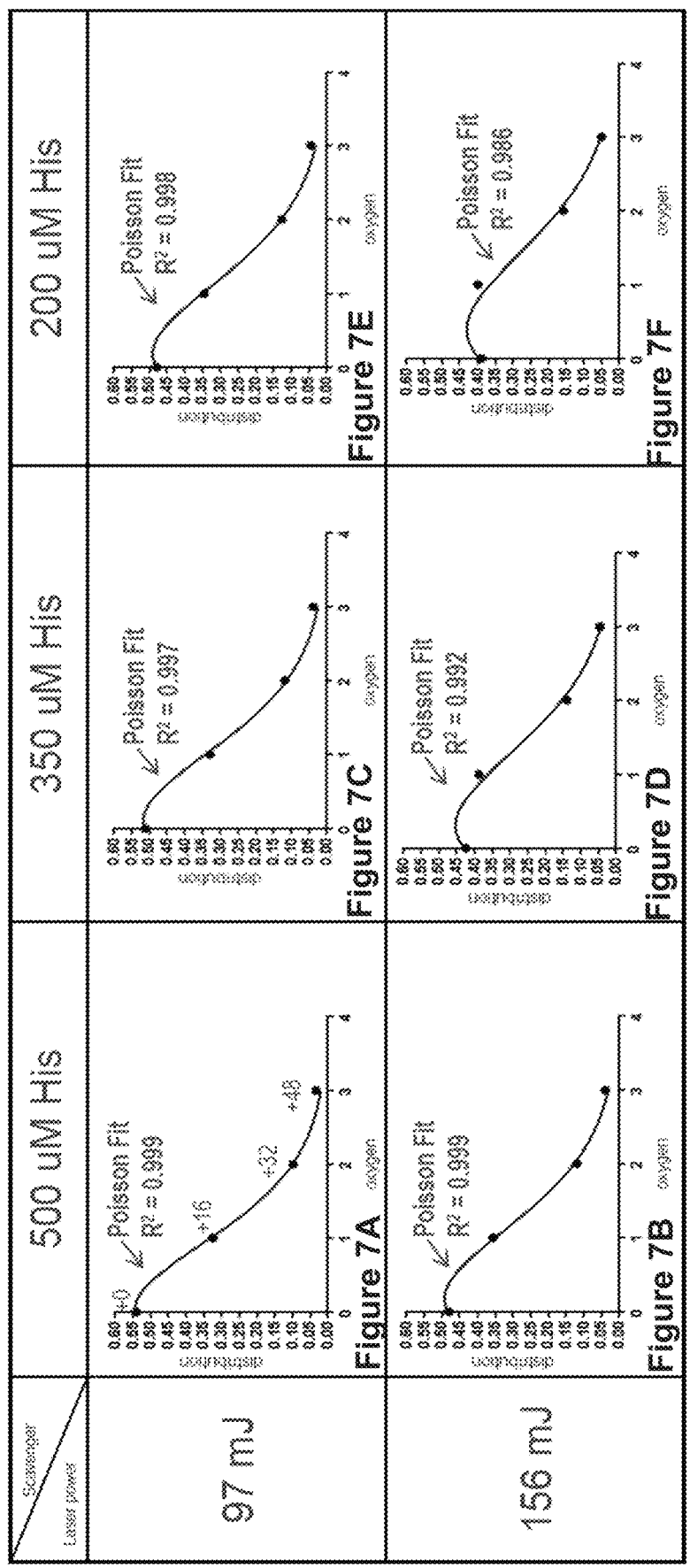

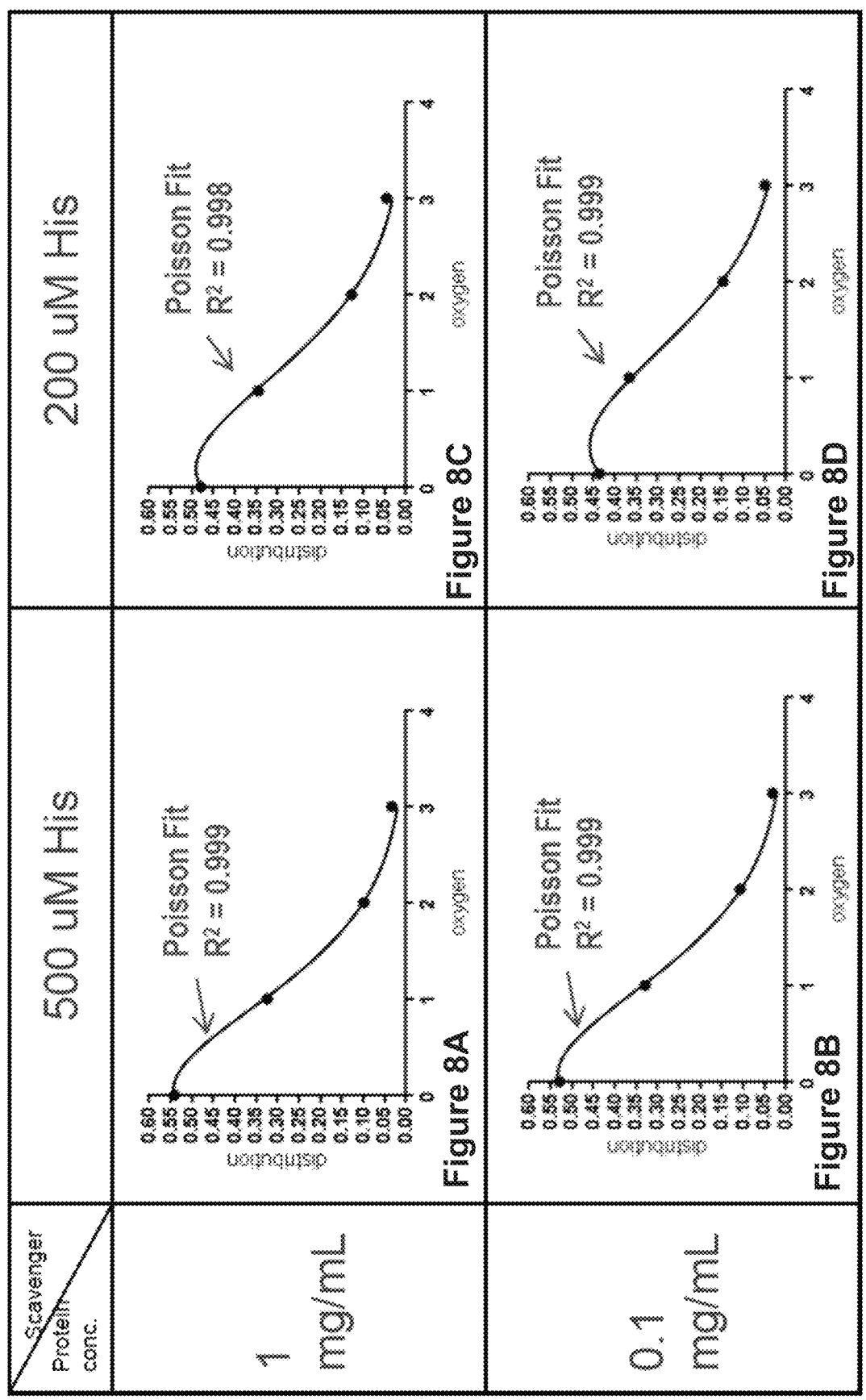

FPOP of mAb1

FPOP of deglycosylated mAb1 (w/o buffer exchange)

SYSTEM AND METHOD FOR CHARACTERIZING PROTEIN DIMERIZATION

CROSS-REFERENCE TO RELATED APPLICATIONS

This application claims benefit of and priority to U.S. Provisional Patent Application Nos. 62/625,732 filed on Feb. 2, 2018, and 62/738,051 filed on Sep. 28, 2018, both of which are hereby incorporated by reference in their entireties.

FIELD OF THE INVENTION

The invention is generally directed to analytical methods and systems for characterizing noncovalent interaction sites in proteins and fragments thereof.

BACKGROUND OF THE INVENTION

Monoclonal antibodies (mAbs) have been successfully employed to target a wide range of therapeutic areas over the last two decades (Walsh G., Nature biotechnology 2014; 32:992-1000; Lawrence S. Nature biotechnology 2007; 25:380-2). Protein aggregation remains a major concern in the production of monoclonal antibodies and other therapeutic proteins. Due to potential impact on potency and immunogenicity, it is important to understand the aggregation mechanism so that appropriate control strategies can be implemented to assure product quality.

Mapping the dimerization interface in mAb molecules remain challenging, due to the complexity and heterogeneity of mAb dimers. Although hydrogen-deuterium exchange mass spectrometry (HDX MS) has been successful in studying protein-protein interactions, little success has been achieved in revealing the mAb dimerization interface, presumably due to the method limitations in detecting protein side-chain interactions.

Thus, it is an object of the invention to provide systems and methods for mapping heterogeneous dimerization interfaces of proteins.

It is another object of the invention to provide protein drug products with reduced levels of dimerization.

It is still another object of the invention to provide methods of producing protein drug products having reduced dimerization.

SUMMARY OF THE INVENTION

Systems and methods to characterize protein dimerization interfaces at the peptide/residue level of a protein are provided. An exemplary method includes digesting a protein dimer sample into subdomains, labeling the digested protein sample mixture, isolating labeled dimeric and monomeric subdomain fragments, and peptide mapping the labeled sample to determine and compare the labeling extent in the dimer and in the monomer. Regions that show decreased labeling extents in the dimer fraction than that in the monomer fraction are likely involved or in close proximity to the dimerization interface.

In one embodiment noncovalent dimers were isolated and analyzed by peptide mapping to locate noncovalent interaction sites. In another embodiment to localize the noncovalent dimerization interface at peptide/residue level, the enriched mAb dimer sample was digested into a mixture of F(ab) [or F(ab')] homodimer, F(ab) [or F(ab')] and Fc monomers, and subjected to a labeling experiment, followed by fractionation, tryptic digestion and LC-MS analysis for labeling extent quantitation and comparison at peptide/residue levels. More detail in the steps of the disclosed methods is provided below.

Still another embodiment provides a method of producing an antibody, including the steps of culturing cells producing the antibody in a cell culture, obtaining a sample from the cell culture, characterizing dimerization interfaces in the antibody sample according to the method described above and modifying one or more culture conditions of the cell culture to reduce the amount of dimerization or noncovalent interaction/aggregation of the antibody produced during cell culture. In some embodiments, the sample is taken during the cell culture at any interval. In other embodiments, the sample is taken following production culture, following protein harvest or following purification. The one or more conditions of the cell culture that are changed to reduce the amount of dimerization or aggregation can be selected from the group consisting of temperature, pH, cell density, amino acid concentration, osmolality, growth factor concentration, agitation, gas partial pressure, surfactants, or combinations thereof. The cells can be eukaryotic or prokaryotic. The cells can be Chinese Hamster Ovary (CHO) cells (e.g. CHO K1, DXB-11 CHO, Veggie-CHO), COS cells (e.g. COS-7), retinal cells, Vero cells, CV1 cells, kidney cells (e.g. HEK293, 293 EBNA, MSR 293, MDCK, HaK, BHK21), HeLa cells, HepG2 cells, WI38 cells, MRC 5 cells, Colo25 cells, HB 8065 cells, HL-60 cells, lymphocyte cells, e.g. autologous T cells, Jurkat (T lymphocytes) or Daudi (B lymphocytes), A431 (epidermal) cells, U937 cells, 3T3 cells, L cells, C127 cells, SP2/0 cells, NS-0 cells, MMT cells, stem cells, tumor cells, and a cell line derived from any of the aforementioned cells. In one embodiment the cells are hybridoma or quadroma cells.

Still another embodiment provides a method of producing an antibody, including the steps of culturing cells producing the antibody in a cell culture, then purifying and formulating the antibody to obtain a formulated drug substance (FDS), obtaining a sample of the purified antibody before and/or after formulating the antibody, characterizing dimerization interfaces in the antibody sample or FDS sample according to the method described above and modifying one or more conditions of the antibody purification or formulation to reduce the amount of dimerization or noncovalent interaction/aggregation of the antibody produced during cell culture. The one or more conditions of the purification of the antibody that are changed to reduce the amount of dimerization or aggregation can be selected from the group consisting of temperature, pH, affinity matrix, chromatography resin, buffers, filters or combinations thereof. The one or more conditions of the formulation of the antibody that are changed to reduce the amount of dimerization or aggregation can be selected from the group consisting of pH, antibody concentration, excipient concentration, buffers, surfactants, stabilizers or any combinations thereof. One or more excipients of the FDS may be changed to reduce the amount of dimerization or aggregation and are selected from any of the known excipients in the art.

Still another embodiment provides an antibody produced by the methods described herein.

Methods for providing modified protein drug products with reduced dimerization or noncovalent interaction relative to an unmodified protein drug product are also provided.

In one embodiment, the protein drug product is a monoclonal antibody or an antigen binding fragment thereof.

BRIEF DESCRIPTION OF THE DRAWINGS

FIGS. 4A-4C are scatter plots showing Poisson fitting of oxidized species for limited LysC digested mAb1 HMW sample. FIG. 4A represents the Fc region, FIG. 4B represents the LC region, and FIG. 4C represents the Fd region. The line represents the Poisson fit for each graph.

FIGS. 7A-7F are scatter plots showing Poisson fitting of oxidized species for lysozyme protein with various concentrations of scavenger (500 µM, 350 µM, or 200 µM His) and various laser power settings (97 mJ or 156 mJ).

FIGS. 8A-8D are scatter plots showing Poisson fitting of oxidized species for lysozyme protein with various concentrations of scavenger (500 µM, or 200 µM His) and various protein concentrations (1 mg/mL or 0.1 mg/mL).

DETAILED DESCRIPTION OF THE INVENTION

I. Definitions

Figure 1:
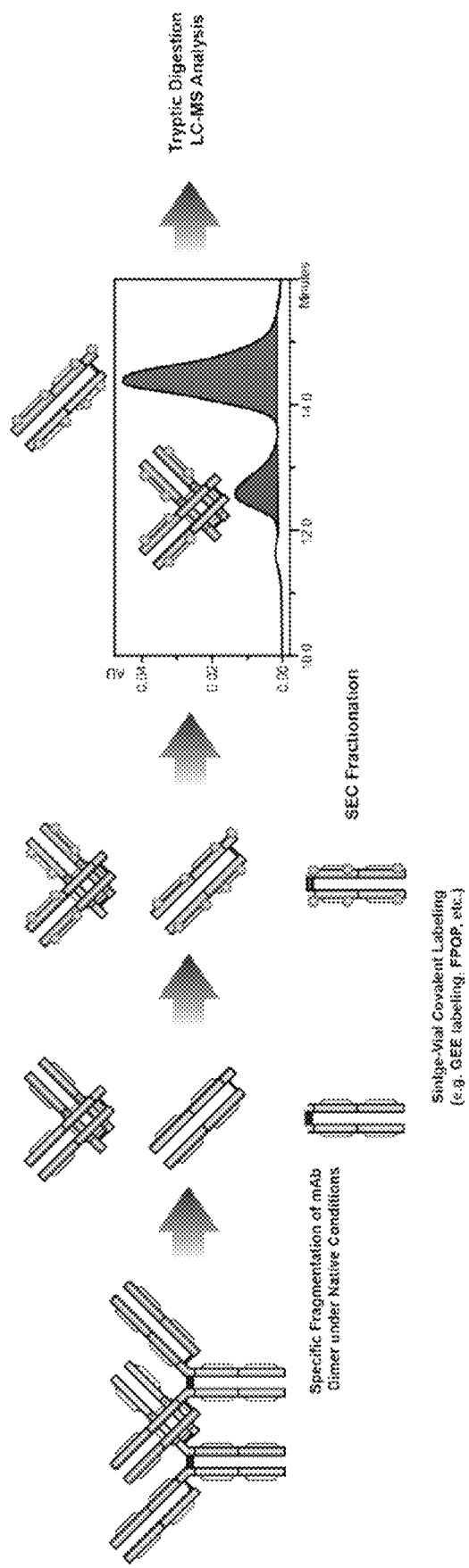
FIG. 1 is a workflow diagram of an exemplary limited digestion and single-labeling strategy for mAb dimerization interface mapping.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

"Protein" refers to a molecule comprising two or more amino acid residues joined to each other by a peptide bond. Protein includes polypeptides and peptides and may also include modifications such as glycosylation, lipid attachment, sulfation, gamma-carboxylation of glutamic acid residues, alkylation, hydroxylation and ADP-ribosylation. Proteins can be of scientific or commercial interest, including protein-based drugs, and proteins include, among other things, enzymes, ligands, receptors, antibodies and chimeric or fusion proteins. Proteins are produced by various types of recombinant cells using well-known cell culture methods, and are generally introduced into the cell by transfection of genetically engineering nucleotide vectors (e.g., such as a sequence encoding a chimeric protein, or a codon-optimized sequence, an intronless sequence, etc.), where the vectors may reside as an episome or be integrated into the genome of the cell.

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains a CH1 domain, a hinge domain, a CH2 domain, and a CH3 domain. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Each VH/CH1 and VL/CL chain associate (e.g. by disulfide bridges) to form a pair, or F(ab), having an antigen-binding site at its N-terminus. Thus, following limited enzyme digestion, a F(ab) [or F(ab')] fragment is an antibody fragment that still binds to antigens but is monovalent with no Fc portion. An antibody is typically bivalent with respect to antigen-binding, and as such includes two F(ab) portions, referred to as F(ab')2, linked together by disulfide bridges in the upper hinge. F(ab')2 fragments are generated by limited digestion of whole antibodies to remove most of the Fc region while leaving intact some of the hinge region, and may be further reduced to F(ab') fragments. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one different epitope. Bivalent antibody structures may also be bispecific with respect to the specificity of each antigen-binding site to different antigens. Bispecific antibodies are generally described in US Patent Application Publication No. 2010/0331527, which is incorporated by reference into this application.

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Ashkenazi et al., Proc. Natl. Acad. ScL USA 88: 10535, 1991; Byrn et al., Nature 344:677, 1990; and Hollenbaugh et al., "Construction of Immunoglobulin Fusion Proteins", in Current Protocols in Immunology, Suppl. 4, pages 10.19.1-10.19.11, 1992. "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein comprises two or more distinct receptor chains that bind to a one or more ligand(s). For example, an Fc-fusion protein is a trap, such as for example an IL-1 trap or VEGF trap.

"Cell culture" refers to the propagation or proliferation of cells in a vessel, such as a flask or bioreactor, and includes but is not limited to fed-batch culture, continuous culture, perfusion culture and the like.

The term "MS/MS" refers to a mass spectrometry technique that uses two mass spectrometers in tandem. Between the two analyzers (MS1 and MS2) is a collision gas cell. Precursor ions selected by MS1 collide with a high pressure gas (usually He) in the cell and undergo fragmentation.

The term "LC-MS" refers to liquid chromatography-mass spectrometry which is an analytical chemistry technique that combines the physical separation capabilities of liquid chromatography (or HPLC) with the mass analysis capabilities of mass spectrometry (MS).

The term "a conservative amino acid substitution" refers to a replacement of an amino acid with another that has similar properties. This type of replacement is expected to rarely result in dysfunction in the corresponding protein.

II. Protein Drug Products

One embodiment provides a protein drug product that has been modified to reduce protein drug product dimerization or noncovalent interaction. The modification can be a conservative amino acid substitution. In a conservative amino acid substitution an amino acid is exchanged into another that has similar properties. This type of replacement is expected to rarely result in dysfunction in the corresponding protein.

A. Proteins of Interest

In one embodiment the protein drug product can contain one or more proteins of interest suitable for expression in prokaryotic or eukaryotic cells. For example, the protein of interest includes, but is not limited to, an antibody or antigen-binding fragment thereof, a chimeric antibody or antigen-binding fragment thereof, an ScFv or fragment thereof, an Fc-fusion protein or fragment thereof, a growth factor or a fragment thereof, a cytokine or a fragment thereof, or an extracellular domain of a cell surface receptor or a fragment thereof. Proteins of interest may be simple polypeptides consisting of a single subunit, or complex multisubunit proteins comprising two or more subunits. The protein of interest may be a biopharmaceutical product, food additive or preservative, or any protein product subject to purification and quality standards.

In some embodiments, the protein product (protein of interest) is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a dual-specific, tetravalent immunoglobulin G-like molecule, termed dual variable domain immunoglobulin (DVD-IG), an IgD antibody, an IgE antibody, an IgM antibody, an IgG antibody, an IgG1 antibody, an IgG2 antibody, an IgG3 antibody, or an IgG4 antibody. In one embodiment, the antibody is an IgG1 antibody. In one embodiment, the antibody is an IgG2 antibody. In one embodiment, the antibody is an IgG4 antibody. In another embodiment, the antibody comprises a chimeric hinge. In still other embodiments, the antibody comprises a chimeric Fc. In one embodiment, the antibody is a chimeric IgG2/IgG4 antibody. In one embodiment, the antibody is a chimeric IgG2/IgG1 antibody. In one embodiment, the antibody is a chimeric IgG2/IgG1/IgG4 antibody.

In some embodiments, the antibody is selected from the group consisting of an anti-Programmed Cell Death 1 antibody (e.g. an anti-PD1 antibody as described in U.S. Pat. Appln. Pub. No. US2015/0203579A1), an anti-Programmed Cell Death Ligand-1 (e.g. an anti-PD-L1 antibody as described in in U.S. Pat. Appln. Pub. No. US2015/0203580A1), an anti-D114 antibody, an anti-Angiopoetin-2 antibody (e.g. an anti-ANG2 antibody as described in U.S. Pat. No. 9,402,898), an anti-Angiopoetin-Like 3 antibody (e.g. an anti-AngPtl3 antibody as described in U.S. Pat. No. 9,018,356), an anti-platelet derived growth factor receptor antibody (e.g. an anti-PDGFR antibody as described in U.S. Pat. No. 9,265,827), an anti-Erb3 antibody, an anti-Prolactin Receptor antibody (e.g. anti-PRLR antibody as described in U.S. Pat. No. 9,302,015), an anti-Complement 5 antibody (e.g. an anti-C5 antibody as described in U.S. Pat. Appln. Pub. No US2015/0313194A1), an anti-TNF antibody, an anti-epidermal growth factor receptor antibody (e.g. an anti-EGFR antibody as described in U.S. Pat. No. 9,132,192 or an anti-EGFRvIII antibody as described in U.S. Pat. Appln. Pub. No. US2015/0259423A1), an anti-Proprotein Convertase Subtilisin Kexin-9 antibody (e.g. an anti-PCSK9 antibody as described in U.S. Pat. No. 8,062,640 or U.S. Pat. Appln. Pub. No. US2014/0044730A1), an anti-Growth And Differentiation Factor-8 antibody (e.g. an anti-GDF8 antibody, also known as anti-myostatin antibody, as described in U.S. Pat. No. 8,871,209 or 9,260,515), an anti-Glucagon Receptor (e.g. anti-GCGR antibody as described in U.S. Pat. Appln. Pub. Nos. US2015/0337045A1 or US2016/0075778A1), an anti-VEGF antibody, an anti-IL1R antibody, an interleukin 4 receptor antibody (e.g an anti-IL4R antibody as described in U.S. Pat. Appln. Pub. No. US2014/0271681A1 or U.S. Pat. No. 8,735,095 or 8,945,559), an anti-interleukin 6 receptor antibody (e.g. an anti-IL6R antibody as described in U.S. Pat. Nos. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (e.g. anti-IL33 antibody as described in U.S. Pat. Appln. Pub. Nos. US2014/0271658A1 or US2014/0271642A1), an anti-Respiratory syncytial virus antibody (e.g. anti-RSV antibody as described in U.S. Pat. Appln. Pub. No. US2014/0271653A1), an anti-Cluster of differentiation 3 (e.g. an anti-CD3 antibody, as described in U.S. Pat. Appln. Pub. Nos. US2014/0088295A1 and US20150266966A1, and in U.S. Application No. 62/222, 605), an anti-Cluster of differentiation 20 (e.g. an anti-CD20 antibody as described in U.S. Pat. Appln. Pub. Nos. US2014/0088295A1 and US20150266966A1, and in U.S. Pat. No. 7,879,984), an anti-CD19 antibody, an anti-CD28 antibody, an anti-Cluster of Differentiation-48 (e.g. anti-CD48 antibody as described in U.S. Pat. No. 9,228,014), an anti-Fel d1 antibody (e.g. as described in U.S. Pat. No. 9,079,948), an anti-Middle East Respiratory Syndrome virus (e.g. an anti-MERS antibody as described in U.S. Pat. Appln. Pub. No. US2015/0337029A1), an anti-Ebola virus antibody (e.g. as described in U.S. Pat. Appln. Pub. No. US2016/0215040), an anti-Zika virus antibody, an anti-Lymphocyte Activation Gene 3 antibody (e.g. an anti-LAG3 antibody, or an anti-CD223 antibody), an anti-Nerve Growth Factor antibody (e.g. an anti-NGF antibody as described in U.S. Pat. Appln. Pub. No. US2016/0017029 and U.S. Pat. Nos. 8,309,088 and 9,353,176) and an anti-Activin A antibody. In some embodiments, the bispecific antibody is selected from the group consisting of an anti-CD3×anti-CD20 bispecific antibody (as described in U.S. Pat. Appln. Pub. Nos. US2014/0088295A1 and US20150266966A1), an anti-CD3×anti-Mucin 16 bispecific antibody (e.g., an anti-CD3×anti-Muc16 bispecific antibody), and an anti-CD3×anti-Prostate-specific membrane antigen bispecific antibody (e.g., an anti-CD3×anti-PSMA bispecific antibody). In some embodiments, the protein of interest is selected from the group consisting of abciximab, adalimumab, adalimumab-atto, ado-trastuzumab, alemtuzumab, alirocumab, atezolizumab, avelumab, basiliximab, belimumab, benralizumab, bevacizumab, bezlotoxumab, blinatumomab, brentuximab vedotin, brodalumab, canakinumab, capromab pendetide, certolizumab pegol, cemiplimab, cetuximab, denosumab, dinutuximab, dupilumab, durvalumab, eculizumab, elotuzumab, emicizumab-kxwh, emtansinealirocumab, evinacumab, evolocumab, fasinumab, golimumab, guselkumab, ibritumomab tiuxetan, idarucizumab, infliximab, infliximab-abda, infliximab-dyyb, ipilimumab, ixekizumab, mepolizumab, necitumumab, nesvacumab, nivolumab, obiltoxaximab, obinutuzumab, ocrelizumab, ofatumumab, olaratumab, omalizumab, panitumumab, pembrolizumab, pertuzumab, ramucirumab, ranibizumab, raxibacumab, reslizumab, rinucumab, rituximab, sarilumab, secukinumab, siltuximab, tocilizumab, tocilizumab, trastuzumab, trevogrumab, ustekinumab, and vedolizumab.

In some embodiments, the protein of interest is a recombinant protein that contains an Fc moiety and another domain, (e.g., an Fc-fusion protein). In some embodiments, an Fc-fusion protein is a receptor Fc-fusion protein, which contains one or more extracellular domain(s) of a receptor coupled to an Fc moiety. In some embodiments, the Fc moiety comprises a hinge region followed by a CH2 and CH3 domain of an IgG. In some embodiments, the receptor Fc-fusion protein contains two or more distinct receptor chains that bind to either a single ligand or multiple ligands. For example, an Fc-fusion protein is a TRAP protein, such as for example an IL-1 trap (e.g., rilonacept, which contains the IL-1RAcP ligand binding region fused to the Il-1R1 extracellular region fused to Fc of hIgG1; see U.S. Pat. No. 6,927,004, which is herein incorporated by reference in its entirety), or a VEGF trap (e.g., aflibercept or ziv-aflibercept, which comprises the Ig domain 2 of the VEGF receptor Flt1 fused to the Ig domain 3 of the VEGF receptor Flk1 fused to Fc of hIgG1; see U.S. Pat. Nos. 7,087,411 and 7,279,159). In other embodiments, an Fc-fusion protein is a ScFv-Fc-fusion protein, which contains one or more of one or more antigen-binding domain(s), such as a variable heavy chain fragment and a variable light chain fragment, of an antibody coupled to an Fc moiety.

B. Methods of Producing Proteins

In one embodiment the protein drug product is produced in a fed-batch cell culture. In protein production, a "fed-batch cell culture" or "fed-batch culture" refers to a batch culture wherein the cells and culture medium are supplied to the culturing vessel initially, and additional culture nutrients are slowly fed, in discrete increments, to the culture during culturing, with or without periodic cell and/or product harvest before termination of culture. Fed-batch culture includes "semi-continuous fed-batch culture" wherein periodically whole culture (which may include cells and medium) is removed and replaced by fresh medium. Fed-batch culture is distinguished from simple "batch culture" whereas all components for cell culturing (including the animal cells and all culture nutrients) are supplied to the culturing vessel at the start of the culturing process in batch culture. Fed-batch culture may be different from "perfusion culture" insofar as the supernatant is not removed from the culturing vessel during a standard fed-batch process, whereas in perfusion culturing, the cells are restrained in the culture by, e.g., filtration, and the culture medium is continuously or intermittently introduced and removed from the culturing vessel. However, removal of samples for testing purposes during fed-batch cell culture is contemplated. The fed-batch process continues until it is determined that maximum working volume and/or protein production is reached, and protein is subsequently harvested.

One embodiment provides a protein drug product that is produced in a continuous cell culture. The phrase "continuous cell culture" relates to a technique used to grow cells continually, usually in a particular growth phase. For example, if a constant supply of cells is required, or the production of a particular protein of interest is required, the cell culture may require maintenance in a particular phase of growth. Thus, the conditions must be continually monitored and adjusted accordingly in order to maintain the cells in that particular phase.

The cell cultures used to produce the protein drug product include a cell culture medium. The terms "cell culture medium" and "culture medium" refer to a nutrient solution used for growing mammalian cells that typically provides the necessary nutrients to enhance growth of the cells, such as a carbohydrate energy source, essential (e.g. phenylalanine, valine, threonine, tryptophan, methionine, leucine, isoleucine, lysine, and histidine) and nonessential (e.g. alanine, asparagine, aspartic acid, cysteine, glutamic acid, glutamine, glycine, proline, serine, and tyrosine) amino acids, trace elements, energy sources, lipids, vitamins, etc. Cell culture medium may contain extracts, e.g. serum or peptones (hydrolysates), which supply raw materials that support cell growth. Media may contain yeast-derived or soy extracts, instead of animal-derived extracts. Chemically defined medium refers to a cell culture medium in which all of the chemical components are known (i.e. have a known chemical structure). Chemically defined medium is entirely free of animal-derived components, such as serum- or animal-derived peptones. In one embodiment, the medium is a chemically defined medium.

The solution may also contain components that enhance growth and/or survival above the minimal rate, including hormones and growth factors. The solution may be formulated to a pH and salt concentration optimal for survival and proliferation of the particular cell being cultured.

A "cell line" refers to a cell or cells that are derived from a particular lineage through serial passaging or subculturing of cells. The term "cells" is used interchangeably with "cell population".

The term "cell" includes any cell that is suitable for expressing a recombinant nucleic acid sequence. Cells include those of prokaryotes and eukaryotes, such as bacterial cells, mammalian cells, human cells, non-human animal cells, avian cells, insect cells, yeast cells, or cell fusions such as, for example, hybridomas or quadromas. In certain embodiments, the cell is a human, monkey, ape, hamster, rat or mouse cell. In other embodiments, the cell is selected from the following cells: Chinese Hamster Ovary (CHO) (e.g. CHO K1, DXB-11 CHO, Veggie-CHO), COS (e.g. COS-7), retinal cell, Vero, CV1, kidney (e.g. HEK293, 293 EBNA, MSR 293, MDCK, HaK, BHK21), HeLa, HepG2, WI38, MRC 5, Colo25, HB 8065, HL-60, lymphocyte, e.g. Jurkat (T lymphocyte) or Daudi (B lymphocyte), A431 (epidermal), U937, 3T3, L cell, C127 cell, SP2/0, NS-0, MMT cell, stem cell, tumor cell, and a cell line derived from an aforementioned cell. In some embodiments, the cell comprises one or more viral genes, e.g. a retinal cell that expresses a viral gene (e.g. a PER.C6® cell). In some embodiments, the cell is a CHO cell. In other embodiments, the cell is a CHO K1 cell.

Methods of purifying proteins are well-known in the art. The drug product may be subject to a number of purification steps following cell culture and harvest of the protein to remove impurities, including host cell proteins and aberrant forms of the drug product, associated with the cell culture process. Forms of chromatography are well-known, such as "affinity chromatography" which is a chromatographic method that makes use of the specific, reversible interactions between proteins rather than general properties of the protein such as isoelectric point, hydrophobicity, or size, to effect chromatographic separation. "Protein A affinity chromatography" or "Protein A chromatography" refers to a specific affinity chromatographic method that makes use of the affinity of the IgG binding domains of Protein A for the Fc portion of an immunoglobulin molecule. This Fc portion comprises human or animal immunoglobulin constant domains CH2 and CH3 or immunoglobulin domains substantially similar to these. Other forms of chromatography or separation techniques include, but are not limited to: Protein G affinity chromatography, His-Tagged affinity chromatography, Ion-Exchange (Weak Cation, Weak Anion, Strong Cation, Strong Anion) chromatography, Size Exclusion chromatography, Reverse Phase chromatography, Normal Phase chromatography, Hydrophobic Interaction Chromatography, Hydrophilic Interaction Chromatography. Each technique requires optimization of suitable conditions including, but are not limited to, resin charge and size, wash conditions, pH, load volume, load concentration, and the like. Ultrafiltration and diafiltration techniques are also contemplated in the purification process.

Methods of formulating proteins are well-known in the art. The drug products of the present invention include liquid pharmaceutical compositions comprising the antigen-binding molecules (e.g., an antibody) of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. For example, the excipients can include a stabilizer, a buffer, a tonicifier, a surfactant, an organic solvent, a salt or a combination thereof. In some embodiments the stabilizer is selected from the group consisting of a polyol, a sugar, an amino acid, a non-ionic surfactant, and a combination thereof. In some embodiments the tonicifier is selected from the group consisting of a sugar, an amino acid, a salt, and a combination thereof. In some embodiments, the drug product is a liquid formulation or a reconstituted lyophilized formulation of the drug product. In some embodiments, the drug product is a co-formulation which comprises two or more different antibodies.

III. Methods for Characterizing Dimerization Interfaces in Proteins

Protein aggregation remains a major concern in the production of monoclonal antibodies. Due to potential impact on purity, potency and immunogenicity, it is important to understand the aggregation mechanism so that appropriate control strategies can be implemented to assure product quality. Mapping the dimerization interface in a mAb molecule remains challenging, due to the complexity and heterogeneity of mAb dimers. Although hydrogen-deuterium exchange mass spectrometry (HDX MS) has been successful in studying protein-protein interactions, little success has been achieved in revealing the mAb dimerization interface, presumably due to the method limitations in detecting protein side-chain interactions.

To overcome these obstacles, new systems and methods are provided for successful mapping of the heterogeneous dimerization interfaces (both covalent and non-covalent) of a protein by comprehensive MS-based methods. An exemplary strategy for dimerization interface mapping is provided in FIG. 1. The protein can be an antibody or antigen binding fragment thereof, a recombinant protein, or a fusion protein.

A. Methods of Characterizing Noncovalent Interaction Sites

One embodiment provides a method to determine the dimerization interfaces at the peptide/residue level of a protein. An exemplary method includes digesting a protein dimer sample into subdomains, labeling the digested protein sample mixture, isolating labeled dimeric and monomeric subdomain fragments, and peptide mapping the labeled sample to determine and compare the labeling extent in the dimer and in the monomer. Regions that show decreased labeling extents in the dimer fraction than that in the monomer fraction are likely involved or in close proximity to the dimerization interface.

In one embodiment peptides were isolated and analyzed by peptide mapping to locate noncovalent interaction sites. In another embodiment to localize the noncovalent dimerization interface at peptide/residue level, the enriched mAb dimer sample was digested into a mixture of F(ab) [or F(ab')] homodimer, F(ab) [or F(ab')] and Fc monomers, then subjected to a covalent labeling experiment, followed by SEC-fractionation, tryptic digestion and LC-MS analysis for labeling extent quantitation and comparison at peptide/residue levels. In still another embodiment to localize the noncovalent dimerization interface at peptide/residue level, the enriched mAb dimer sample was digested into a mixture of F(ab) [or F(ab')] homodimer, F(ab) [or F(ab')] and Fc monomers, then subjected to a single FPOP (fast photochemical oxidation of proteins) labeling experiment, followed by SEC-fractionation, tryptic digestion and LC-MS analysis for labeling extent quantitation and comparison at peptide/residue levels. More detail in the steps of the disclosed methods is provided below.

1. Fragmentation of Protein Dimers

In one embodiment, a protein drug product, for example an antibody, is obtained from a cell culture and enriched for dimers to provide an enriched dimer sample. The enriched dimer sample can be produced using a variety of enrichment techniques including but not limited to liquid chromatography. A preferred liquid chromatography technique includes but is not limited to size exclusion chromatography. In some embodiments, the enriched dimer sample contains some protein aggregates other than dimers. Thus, the enriched dimer sample need not be composed of only dimers. In one embodiment, the enriched dimer sample contains more than 50% dimers.

Fragmentation or digestion of a protein product, for example to preserve the noncovalent interactions forming a mAb dimer, can be accomplished using conventional techniques often called limited digestion, including chemical and enzymatic techniques. In one embodiment, a mAb dimer sample is digested under native conditions to produce various Fab and Fc fragments, e.g. a mixture of F(ab) homodimer, F(ab) and Fc monomers, using a protease. An exemplary protease is endoprotease LysC. Other proteases include papain and ficain. In one embodiment, the mAb dimer can be diluted in 10 mM Tris-HCl (pH 7.5) and then incubated with endoprotease Lys-C (Protein:enzyme=400: 1). This limited digestion treatment specifically cleaves the heavy chain at a Lys residue which is the N-terminal to the two hinge region disulfide bonds leading to the generation of Fab and Fc fragments. Any noncovalent dimer interactions (most commonly F(ab)-F(ab)) from the dimer species are maintained in the mixture.

In another embodiment, the mAb dimer sample is digested into F(ab')2 and Fc* fragments (i.e. two Fc polypeptides that interact by noncovalent interactions, referred to herein as Fc monomers) under native conditions with IdeS protease sold under the name FabRICATOR®. mAb dimer can first be diluted in 10 mM Tris-HCl (pH 8.0) and then digested with FabRICATOR® (1 TUB milliunit per 1 μg of protein). This limited digestion treatment specifically cleaves between two Gly residues, a site that is C-terminal to the two hinge region disulfide bonds. This treatment can result in the generation of one F(ab')2 fragment and two identical Fc/2 fragments that are bound together through non-covalent interactions (Fc*). The digestion mixture can then be incubated with a reducing agent, which reduces the inter-chain disulfide bonds while maintaining the intra-chain disulfide bonds intact. As a result, the F(ab')2 fragments are reduced into two F(ab') fragments and the Fd and LC are bound together through noncovalent interaction. The noncovalent dimer interactions (most commonly F(ab')-F(ab')) from the dimer species are also maintained in the mixture.

Exemplary reducing agents that can be used include but are not limited to dithiothreitol (DTT, CAS 3483-12-3), beta-mercaptoethanol (BME, 2BME, 2-ME, b-mer, CAS 60-24-2), 2-aminoethanethiol (2-MEA-HCl, also called cysteamine-HCl, CAS 156-57-0), Tris (2-carboxyethyl) phosphine hydrochloride, (TCEP, CAS 5961-85-3), cysteine hydrochloride (Cys-HCl, CAS 52-89-1), or 2-mercaptoethanesulfonic acid sodium salt (MESNA). Other methods for reducing protein bonds are known in the art, such as an immobilized reductant column which contains resin to which a thiol-based reducing agent has been immobilized to enable the solid-phase reduction of peptide and protein disulfide bonds. Reducing agents, including oxidizing agents, which are suitable for reducing chemical interaction between polypeptides are also envisioned.

2. Labeling Protein Fragments i. Carboyxl Group Labeling

In one embodiment, the digested mAb sample is labeled using carboxyl group labeling. Carboxyl group footprinting is a commonly used covalent labeling technique to study protein conformation and interactions by labeling the sidechains of Asp and Glu residues with glycine ethyl ester hydrochloride (GEE). In the GEE labeling reaction, carboxyl groups from Asp and Glu residues located on the surface of a protein are readily modified, whereas ones buried in the interior of the protein structure undergo less or even no modifications. In one embodiment the digested sample can be mixed with 0.2 M 1-ethyl-3-[3-dimethylaminopropyl] carbodiimide hydrochloride (EDC) and 2 M GEE and incubated at room temperature for 1 hour. The GEE labeling reaction can be quenched by the addition of 1M Tris-HCl (pH 8). In one embodiment, the sample solution can then be concentrated. Methods of concentrating samples are well-known in the art. Exemplary methods include but are not limited to membrane dialysis, precipitation or salting out, cellulose membrane concentrators, and centrifugation. In a preferred embodiment, the sample is concentrated by centrifugation using for example an Ultracel-10K centrifugal filter.

ii. Fast Photochemical Oxidation of Proteins (FPOP)

In one embodiment the digested mAb sample is label using FPOP. FPOP is a well-developed hydroxyl radical labeling method that labels the protein at the amino acid residue side chain at μs time scale, and has been widely applied in studying protein-protein/ligand interactions. In one embodiment the digested mAb dimer containing mAb fragments and non-covalently linked fragment dimers are buffer exchanged into an appropriate buffer, for example PBS (pH 7.4). Buffer exchange can be necessary because quenchers react quickly with OH radicals and should be avoided during labeling. Common quenchers include but are not limited to certain buffer solutions such as Tris-HCl and chemicals such as glycerol and DTT.

.OH labeling can cause conformational changes to the native conformation of the protein. In one embodiment, scavengers can be used to control the OH radical lifetime so the protein does not get over-labeled, ensuring that the native conformation is captured and not an over-labeled protein with conformational changes. Exemplary scavengers that can be used include but are not limited to Cys, Trp, Tyr, Met, His, Phe, Arg, Ile, Leu, Val, Pro, Gln, Thr, and Lys. In a preferred embodiment, the scavenger is His. The buffer exchanged mixture can first be mixed with PBS and concentrated scavenger solution and $H_2O_2$ stock solution. His can be added at a concentration of 200-500 μM. The His concentration can be 200, 225, 250, 275, 300, 325, 350, 375, 400, 425, 450, 475, or 500 μM. An exemplary mixture contains 1 mg/mL mAb digestion mixture, 350 μM His and 20 mM $H_2O_2$ to make a final 100 μL of solution. In one embodiment, $H_2O_2$ can be added just prior to infusing the solution into the tubing for FPOP.

Oxidative labeling of the protein can be monitored by modeling the intensities of unmodified, +16 Da, +32 Da, and +48 Da species by Poisson distribution. Oxygen-addition state distribution values can be tested for goodness-of-fit to Poisson distribution. In one embodiment, data that do not fit into the predicted Poisson distribution indicate over-labeling of the protein. Alternatively, if the data fit into the Poisson model there is sufficient labeling without over-labeling of the protein.

In one embodiment, the sample can be loaded into a 100 μL gas tight syringe and introduced via a syringe pump coupled to a 150 μm i.d. fused silica tubing. The tubing can have a clear window in the center facing a laser beam. The laser can be an excimer laser, for example a KrF excimer laser. Any commercially available excimer lasers can be used, for example COMPex 50 laser (Coherent Inc.). The KrF excimer laser power can be between about 100 and 150 mJ/pulse. In a preferred embodiment, the laser power can be between about 100 and 120 mJ/pulse. The pulse frequency of the laser can be set to 6 Hz. The width of the laser beam at the clear sample tube window can be from about 1.5 mm to 3.0 mm. The laser width can be 1.5 mm, 1.75 mm, 2 mm, 2.25 mm, 2.5 mm, 2.75 mm, or 3 mm. Laser power can fluctuate over time. Therefore, in one embodiment, the same set of labeling experiments can be performed on the same day for maximum labeling consistency. In another embodiment, dosimeters can be added for monitoring run-to-run labeling efficiency fluctuations.

After turning on the pulsed laser, the sample solution can be infused into the tubing, for example at flow rate of 23.86 µL/min. The flow rate can be adjusted according the tubing i.d., laser frequency, and measured laser beam width. The flow rate should be adequate to ensure a 20% exclusion volume to avoid repeated .OH exposure and reaction. In one embodiment, the capillary outflow can be collected into a vial containing solutions to reduce residual $H_2O_2$. Reduction of residual $H_2O_2$ can be achieved using reducing agents, antioxidants, or a combination thereof. Exemplary non-enzymatic antioxidant agents include but are not limited to vitamin A, vitamin C, vitamin E, beta carotene, carotene, taurine, hypotaurine, glutathione, selenium, zinc, methionine, and ubiquinone. Enzymatic antioxidant agents include but are not limited to SOD, catalase, glutaredoxin, and glutathione reductase. In a preferred embodiment, the solution to reduce residual $H_2O_2$ contains methionine and catalase. The labeled sample outflow solution can be concentrated by centrifugation, for example using an ultracel-10K centrifugal filter.

iii. Isolation of Labeled mAb Fragment Dimers and Monomers

In one embodiment the covalently labeled sample mixture can be separated using size exclusion chromatography, for example a BEH® SEC column. Following the SEC separation and UV detection (280 nm), the dimeric and monomeric fragments can be collected for tryptic peptide mapping analysis.

It is understood that the disclosed methods are not limited to any specific sequence of the steps of fractionation (limited digestion) and labeling as presented herein.

iv. Peptide Mapping of Labeled Dimer Fragments

In one embodiment, the dimer and monomer fractions can be subjected to tryptic peptide mapping. Methods of tryptic peptide mapping are known in the art. In one embodiment, the dimer and monomer fractions can be dried, for example in a SpeedVac and reconstituted in a solution containing 8 M urea, 5 mM dithiothreitol (DTT) and 0.1 M Tris-HCl (pH 7.5) before tryptic peptide mapping. The denatured and reduced samples can be alkylated with 10 mM iodoacetamide (IAA) in the dark for 30 minutes. The sample solutions can then diluted with 0.1 M Tris-HCl (pH 7.5) to lower the urea concentration and digested with trypsin at an enzyme-to-substrate ratio of 1:20 (w/w) at 37° C. overnight. The digestion can be stopped by adding 10% formic acid (FA) to each digested protein sample. The samples can then be separated by reverse phase UPLC followed by online mass spectrometric analysis to determine the peptide masses and confirm peptide identities. In one embodiment, MS and MS/MS experiments are conducted on a Thermo Q Exactive Plus MS system with higher-energy collisional dissociation (HCD) employed for peptide fragmentation during MS/MS experiments.

v. Identification and Characterization of Dimerization Interfaces

In one embodiment for carboxylic group labeling, in order to identify GEE labeled tryptic peptides, the LC-MS/MS data is searched against a database or search engine containing the corresponding mAb protein sequence with variable modifications of GEE1 (+85.0522) and GEE2 (+57.0209) restricted to Asp and Glu residues, for example utilizing software such as BYONIC™ (Protein Metrics). To quantitate the GEE labeling extent on each tryptic peptide containing Asp/Glu residue, the extracted ion chromatograms (EICs), based on the m/z of the first isotope peak of both the GEE labeled peptide and native peptide are generated and the extracted peak areas are integrated. The percentage of each GEE labeled peptide is calculated using the corresponding EIC peak area relative to the sum of the peak areas of the labeled and native peptides. In the case of a tryptic peptide containing multiple Asp and Glu residues, GEE labeled peptides eluting at different retention times are first examined for MS/MS spectra to confirm the labeling sites, and then the corresponding EIC peak areas are used to calculate the site-specific labeling percentage. Finally, the GEE labeling extents are compared between the dimer fraction and the monomer fraction for each tryptic peptide or residue. Regions that show decreased labeling extents in the dimer fraction than that in the monomer fraction are likely involved or in close proximity to the dimerization interface.

In one embodiment for FPOP labeling, the LC-MS/MS data are first searched against a database containing the corresponding mAb protein sequence with all known oxidative labeling products (Table 1) to identify all labeling products/peptides. Modification sites on the peptide are identified on the basis of MS/MS information and confirmed by accurate m/z, and the modification extent for a certain peptide was calculated as:

$$\text{Extent of Modification} = \frac{\sum I_{ox}}{\sum I_{ox} + I},$$

Where Iox is the intensity for the modified peptide (Met oxidation excluded due to possible oxidation on Met introduced during non-labeling sample handling) and I is the intensity for the unmodified peptide. Quantitative analysis of oxidative labeling at residue level is also performed for peptides that showed differences in extent of modification at the peptide level between dimers and monomers and peptides containing Met residues. Modification sites on the peptide are assigned with MS2 information. In some embodiments, where location of a modification to a single residue is not possible owing to limited fragmentation information from MS2 or to the presence of interference from co-elution of peptide isomers, the modification is indicated to occur on a set of possible residues. Regions that show decreased labeling extents in the dimer fraction than that in the monomer fraction are likely involved or in close proximity to the dimerization interface.

One embodiment provides a method for identifying non-covalent interaction sites or dimerization interfaces in a protein drug product by digesting the enriched dimer sample of a protein drug product under native limited digestion conditions to form a protein drug mixture sample containing non-covalently linked dimeric subdomains (e.g. F(ab) dimers) and monomeric subdomains, and introducing detectable modifications into the dimers and monomers of the protein drug mixture sample to produce modified dimers and modified monomers. The method includes separating the modified dimers and modified monomers using native size exclusion chromatography into modified dimer and modified monomer fractions and digesting a multitude of peptide bonds of the modified dimer and modified monomer fractions to form digested peptide samples. The method also includes analyzing the digested peptide samples using liquid chromatography/mass spectrometry to obtain mass spectrometry data of the digested peptide samples and determining modification sites in digested peptides in the digested peptide sample using the mass spectrometry data of the digested peptides compared to known mass spectrometry data of the protein drug product having specific residue modifications introduced into the protein drug product.

In one embodiment the dimers and monomers are modified by fast photochemical oxidation to form detectable oxidative modifications into the dimers and monomers. The modification can be an amino acid side chain modification.

As noted above, the protein drug product can be an antibody or an antigen binding fragment thereof, a recombinant protein, a fusion protein, or a combination thereof. A preferred protein drug product is a monoclonal antibody or antigen binding fragment thereof.

In one embodiment, the native size exclusion chromatography is performed using a mobile phase comprising ammonium acetate and ammonium bicarbonate. In another embodiment the digested protein sample is separated with reverse phase liquid chromatography.

In one embodiment, the modification is selected from the group consisting of oxidation, dioxidation, trioxidation, kynurenin, dithiomethyl, decarboxylation, hydrozykynurenin, and combinations thereof.

Typically, the protein drug product is digested with an enzyme, for example digested with protease. Exemplary proteases utilized in limited digestion include, but are not limited to papain, ficain, endoprotease Lys-C and IdeS. Exemplary proteases utilized in peptide bond digestion to form a multitude of peptides include, but are not limited to trypsin, chymotrypsin, pepsin, and rLys-C.

In some embodiments the protein drug product sample is from a fed-batch culture.

B. Methods of Producing Protein Drug Products Having Reduced Noncovalent Interaction or Aggregation One embodiment provides a method of producing an antibody including the steps of culturing cells producing the antibody under suitable conditions to produce the antibody; purifying the antibody under suitable conditions to extract the antibody; admixing the antibody with excipients under suitable conditions to stabilize the antibody; obtaining a sample of the antibody i) from the cell culture, ii) following purification of the antibody from the cell culture, or iii) following the addition of excipients to the purified antibody; characterizing dimerization interfaces in the antibody using the systems and methods disclosed herein and modifying the conditions for producing the antibody or modifying the dimerization interfaces of the antibody to have reduced dimerization and noncovalent interaction relative to an unmodified antibody. Modifying the conditions for producing the antibody are explained hereinabove.

In one embodiment, the modification can be a conservative amino acid substitution or a chemical modification of the of dimerization interfaces.

EXAMPLES

Example 1: Single-Labeling of the Dimer and Monomer Mixture by Covalent Labeling Methods
Limited Digestion of mAb-1
mAb-1, an IgG1 isotype, was digested into F(ab) and Fc fragments under native conditions with endoprotease LysC. A mAb-1 dimer was first diluted to 1 µg/µL in 10 mM Tris-HCl (pH 7.5) and then incubated with endoprotease Lys-C (Protein:enzyme=400:1) at 37° C. for 1 hour. This limited digestion treatment specifically cleaves the heavy chain at a Lys residue which is the N-terminal to the two hinge region disulfide bonds, leading to the generation of both F(ab) and Fc fragments. Any noncovalent dimer interactions (most commonly F(ab)-F(ab)) from the dimer species are maintained in the mixture.

Limited Digestion of mAb-2
mAb-2, and IgG4 isotype, was digested into F(ab')2 and Fc* fragments under native conditions with FabRICATOR®, an IdeS enzyme from Streptocoocus pyogenes. mAb-2 dimer is first diluted to 1 µg/µL in 10 mM Tris-HCl (pH 8.0) and then digested with FabRICATOR® (1 IUB milliunit per 1 of protein) at 37° C. for 1 hour. This limited digestion treatment specifically cleaves between two Gly residues, a site that is C-terminal to the two hinge region disulfide bonds. This treatment resulted in the generation of one F(ab')2 fragment and two identical Fc/2 fragments that bound together through non-covalent interactions (Fc*). The digestion mixture is then incubated with 5 mM of Dithiothreitol (DTT) at 37° C. for 30 minutes, which reduces the inter-chain disulfide bonds while maintaining the intra-chain disulfide bonds intact. As a result, the $Fab_2$ fragments are reduced into two F(ab') fragments and the Fd and LC are bound together through noncovalent interaction. The noncovalent dimer interactions (most commonly F(ab')-F(ab')) from the dimer species are also maintained in the mixture.

The above generated mixture of mAb fragments and non-covalently linked fragment dimers are first buffer exchanged into 1×PBS (pH 7.4) to ~2 mg/mL.

Carboxyl Group Labeling
Carboxyl group footprinting is a commonly used covalent labeling technique to study protein conformation and interactions by labeling the sidechains of Asp and Glu residues with GEE. In the GEE labeling reaction, carboxyl groups from Asp and Glu residues located on the surface of a protein are readily modified, whereas ones buried in the interior of the protein structure undergo less or even no modifications. To perform the labeling, 100 µL of the digested sample of mAb-1 was mixed with 50 µL of 0.2 M 1-ethyl-3-[3-dimethylaminopropyl] carbodiimide hydrochloride (EDC) and 50 µL of 2 M glycine ethyl ester hydrocholoride (GEE) and incubated at room temperature for 1 hour. After quenching the GEE labeling reaction by adding 500 µL of 1M Tris-HCl (pH 8), the sample solution was concentrated by centrifugation using an Ultracel-10K centrifugal filter to about 40 µL.

Fast Photochemical Oxidation of Proteins (FPOP)
FPOP is a well-developed hydroxyl radical labeling method that labels the protein at the amino acid residue side chain at µs time scale, and has been widely applied in studying protein-protein/ligand interactions. In the labeling process, 50 µL of the above buffer exchanged mixture was first mixed with 1×PBS and concentrated His solution and $H_2O_2$ stock solution to make a final 100 µL of solution containing 1 mg/mL mAb-2 digestion mixture, 350 µM His and 20 mM $H_2O_2$. $H_2O_2$ was added just prior to infusing the solution into the tubing for FPOP. The sample was loaded into a 100 µL gas tight syringe and introduced via a syringe pump coupled to the 150 µm i.d. fused silica tubing with a clear window in the center facing the laser beam. The KrF excimer laser power was adjusted to 100-120 mJ/pulse, and its pulse frequency set to 6 Hz. The width of the laser beam at the clear sample tube window was measured to be 3.0 mm. After turning on the pulsed laser, the sample solution was infused into the tubing at flow rate of 23.86 µL/min (adjusted according the tubing i.d., laser frequency, and measured laser beam width) to ensure a 20% exclusion volume to avoid repeated .OH exposure and reaction. The capillary outflow was collected in a vial containing 20 μL of 100 mM Met and 2 μL of 1 mg/mL catalase to reduce residual H₂O₂. Finally, the labeled sample solution was concentrated by centrifugation using an ultracel-10K centrifugal filter to about 40 μL.

SEC/MS

The covalently labeled sample mixture was injected onto a BEH® SEC column (300 mm×4.6 mm, 200 Å, 1.7 μm) that was pre-equilibrated with mobile phase (140 mM ammonium acetate and 10 mM ammonium bicarbonate, pH 7.4) at a flow rate of 0.2 mL/min. Following the SEC separation and UV detection (280 nm), the dimeric and monomeric fragments were collected for tryptic peptide mapping analysis.

Peptide Mapping

Before tryptic digestion, all the dimer and monomer fractions were dried in a SpeedVac and reconstituted in a solution containing 8 M urea, 5 mM dithiothreitol (DTT) and 0.1 M Tris-HCl (pH 7.5) and kept at 50° C. for 30 minutes. The denatured and reduced samples were alkylated with 10 mM iodoacetamide (IAA) in the dark for 30 minutes. The sample solutions were then diluted ten times with 0.1 M Tris-HCl (pH 7.5) to lower the urea concentration to 0.8 M and digested with trypsin at an enzyme-to-substrate ratio of 1:20 (w/w) at 37° C. for overnight. The digestion was then stopped by adding 10% FA to make final 0.2% FA. Aliquots (~5 μg) of each digested protein sample were then separated by reverse phase UPLC followed by online mass spectrometric analysis to determine the peptide masses and confirm peptide identities. MS and MS/MS experiments were conducted on a Thermo Q Exactive Plus MS system with higher-energy collisional dissociation (HCD) employed for peptide fragmentation during MS/MS experiments.

Results

Carboxyl Group Labeling

Figure 2:
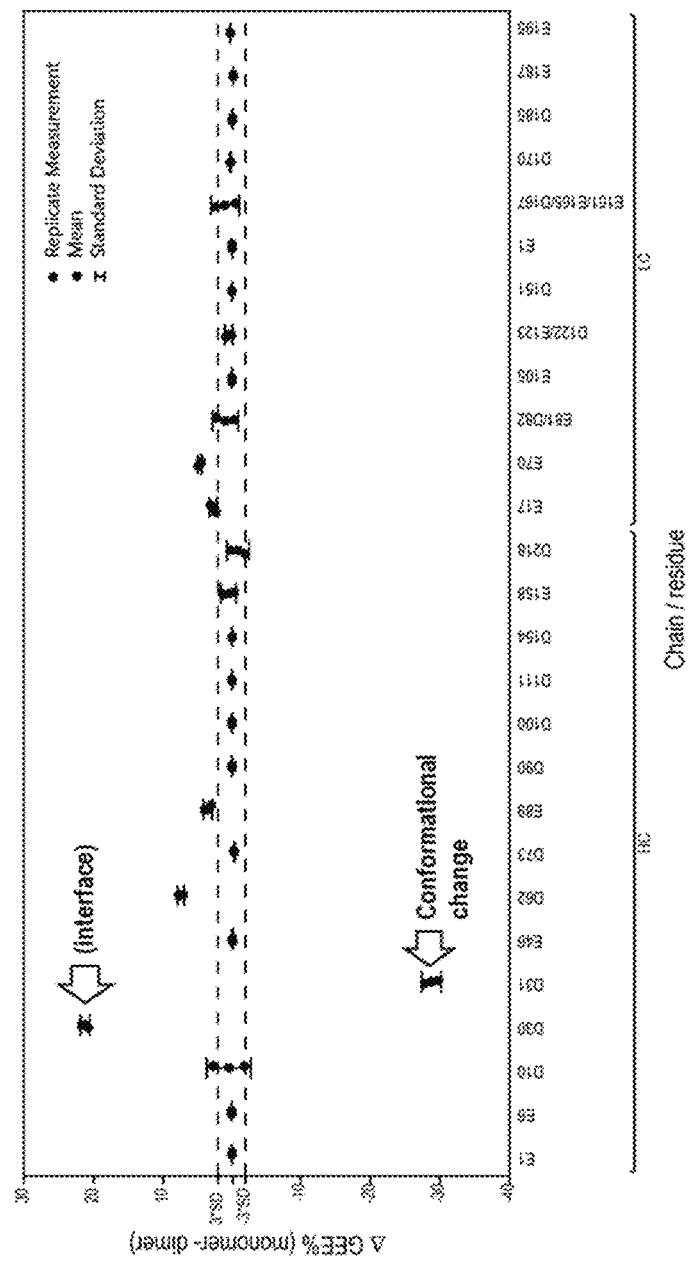
FIG. 2 is a graph of percent glycine ethyl ester hydrocholoride (GEE) (monomer-dimer) for the indicated chain/residue showing differential GEE labeling chart between mAb-1 Fab dimer and Fab monomer generated from limited Lys-C digestion of the enriched HMW sample.
Figure 3A:
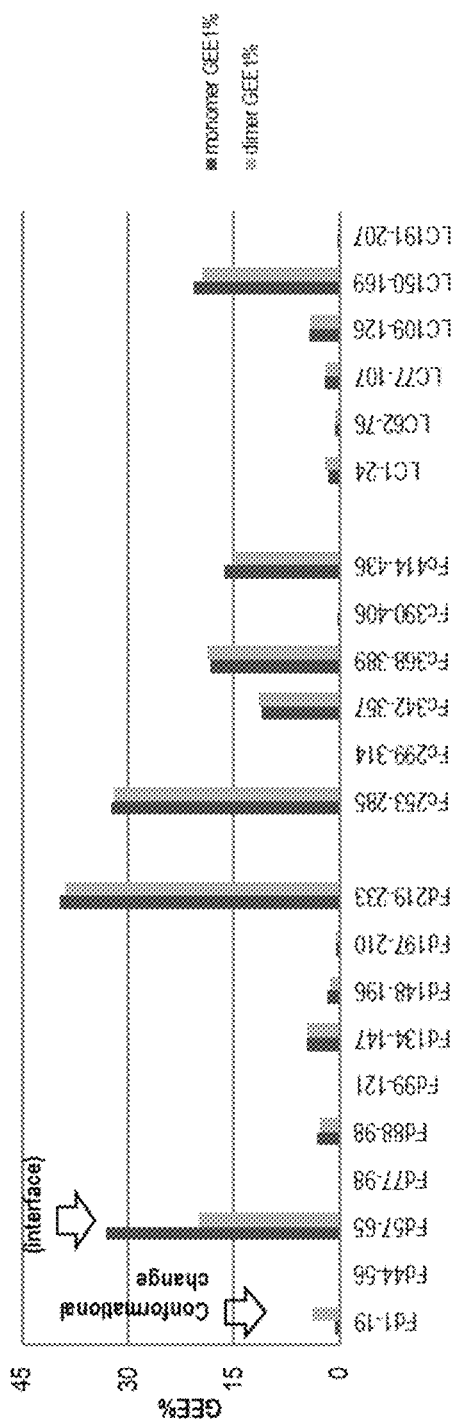
FIG. 3A is a bar graph of GEE percent for the indicated antibody fragment of mAb-1 at the peptide level.
Figure 3B:
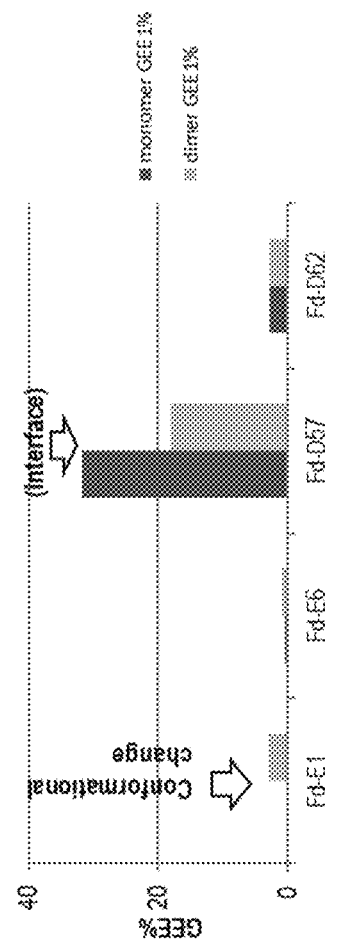
FIG. 3B is a bar graph of GEE percent for the indicated antibody fragment of mAb-2 at the amino acid residue level.

For carboxylic group labeling, in order to identify GEE labeled tryptic peptides, the LC-MS/MS data were searched against a database containing the corresponding mAb protein sequence with variable modifications of GEE1 (+85.0522) and GEE2 (+57.0209) restricted to Asp and Glu residues. To quantitate the GEE labeling extent on each tryptic peptide containing Asp/Glu residue, the extracted ion chromatograms (EICs), based on the m/z of the first isotope peak of both the GEE labeled peptide and native peptide, were generated and the extracted peak areas were integrated. The percentage of each GEE labeled peptide was calculated using the corresponding EIC peak area relative to the sum of the peak areas of the labeled and native peptides. In the case of a tryptic peptide containing multiple Asp and Glu residues, GEE labeled peptides eluting at different retention times were first examined for MS/MS spectra to confirm the labeling sites, and then the corresponding EIC peak areas were used to calculate the site-specific labeling percentage. Finally, the GEE labeling extents were compared between the dimer fraction and the monomer fraction for each tryptic peptide or residue. Regions that show decreased labeling extents in the dimer fraction than that in the monomer fraction are likely involved or in close proximity to the dimerization interface (FIGS. 2, 3A, and 3B).

FPOP Labeling

Figure 5A:
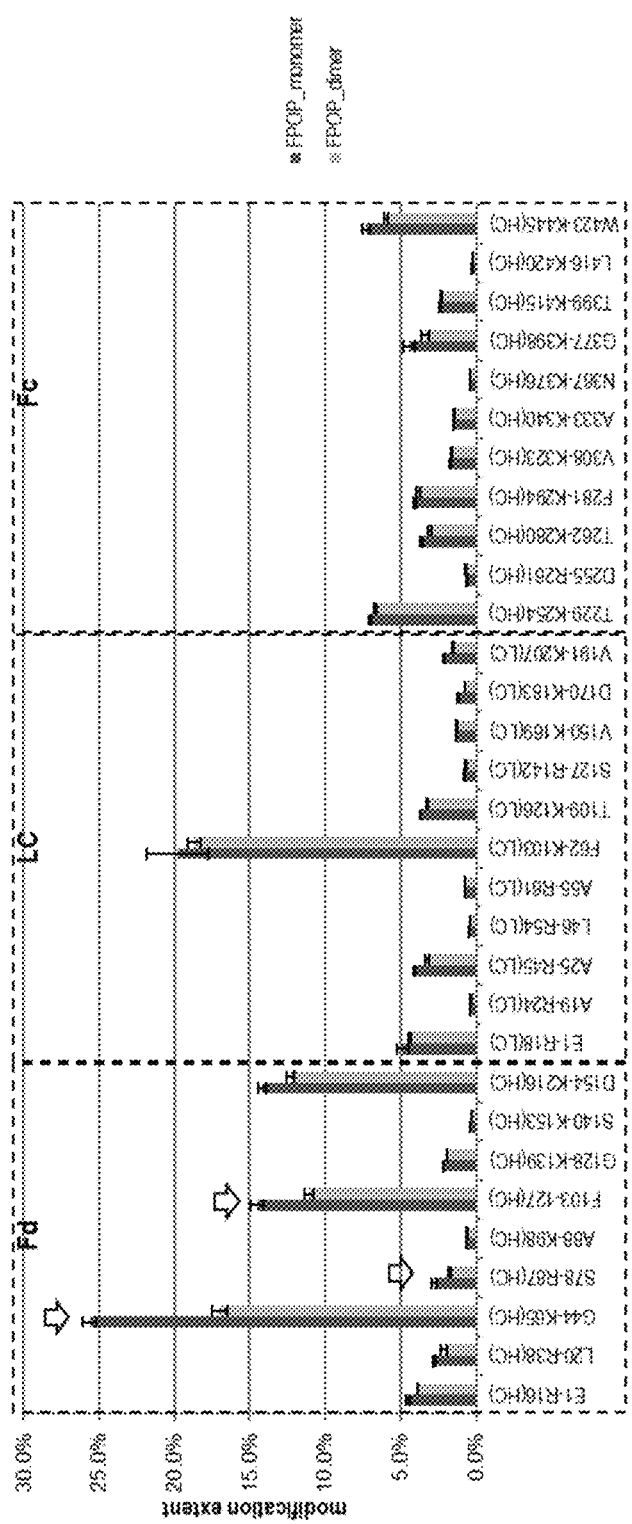
FIG. 5A is a bar graph of FPOP modification extent for the indicated fragment at the peptide level of mAb-1.
Figure 5B:
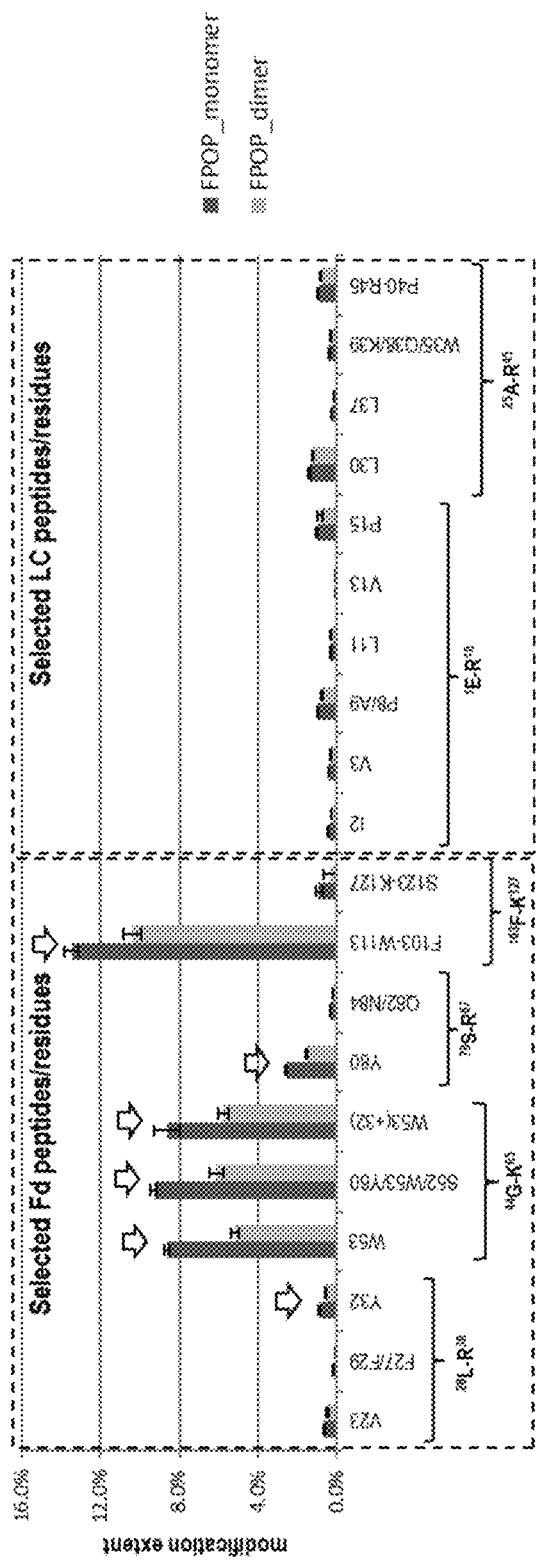
FIG. 5B is a bar graph of FPOP modification extent for the indicated fragment at the residue level of mAb-1.

For FPOP labeling, the LC-MS/MS data were first searched against a database containing the corresponding mAb protein sequence with all known oxidative labeling products (Table 1) to identify all labeling products. Modification sites on the peptide were identified on the basis of MS/MS information and confirmed by accurate m/z, and the modification extent for a certain peptide was calculated as:

$$\text{Extent of Modification} = \frac{\sum I_{ox}}{\sum I_{ox} + I},$$

Where $I_{ox}$ is the intensity for the modified peptide (Met oxidation excluded due to possible oxidation on Met introduced during non-labeling sample handling) and I is the intensity for the unmodified peptide. Quantitative analysis of oxidative labeling at residue level was also performed for peptides that showed differences in extent of modification at the peptide level between dimers and monomers and peptides containing Met residues. Modification sites on the peptide were assigned with MS2 information. In a few cases, where location of a modification to a single residue wasn't possible owing to limited fragmentation information from MS2 or to the presence of interference from co-elution of peptide isomers, the modification was indicated to occur on a set of possible residues. The Poisson distribution of the +0, +16, +32, +48, etc. labeling species at subdomain level indicates no over-labeling occurred (FIGS. 4A-4C). Regions that show decreased labeling extents in the dimer fraction than that in the monomer fraction are likely involved or in close proximity to the dimerization interface (FIGS. 5A and 5B).

TABLE 1

Possible oxidative labeling products.

| | modification | Reactive residues | Mass change |
|---|---|---|---|
| Common | Oxidation | M, C, H, W, F, Y, I, L, V, R, K, E, Q, D, N, S, A, P | +15.9949 |
| | Dioxidation | M, C, W, Y, F | +31.9898 |
| | Trioxidation | C, W, Y, F | +47.9847 |
| | Kynurenine | W | +3.9949 |
| | Carbonylation | W, I, L, P, K, E, Q, V, R | +13.9793 |
| | M + 34 | M | +33.9691 |
| Rare | H − 22 | H | −22.0320 |
| | H − 23 | H | −23.0160 |
| | H − 10 | H | −10.0320 |
| | H − 66 | H | −66.0218 |
| | H + 5 | H | +4.9789 |
| | C − 16 | C | −15.9772 |
| | M − 32 | M | −32.0085 |
| | R − 43 | R | −43.0534 |
| | Dethiomethyl | M | −48.0034 |
| | ST − 2 | S, T | −2.0157 |
| | Decarboxylation | D, E, P | −30.0106 |
| | Pro->Glu | P | +31.9898 |
| | Hydroxykynurenine | W | +19.9898 |

Example 2: FPOP Optimization

Methods:

The FPOP protocol from Example 1 was followed. Various components of the protocol, i.e. laser position, scavenger concentration, and inclusion of quenchers were manipulated to determine their effect on the assay.

Figure 6B:
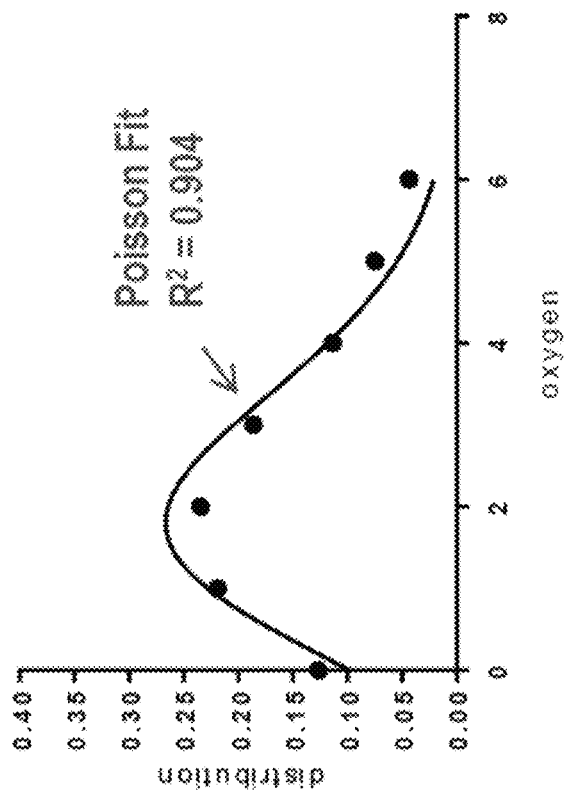
FIGS. 6A and 6B are scatter plots showing Poisson fitting of oxidized species for lysozyme protein with different focus position and laser power conditions.
Figure 6A:
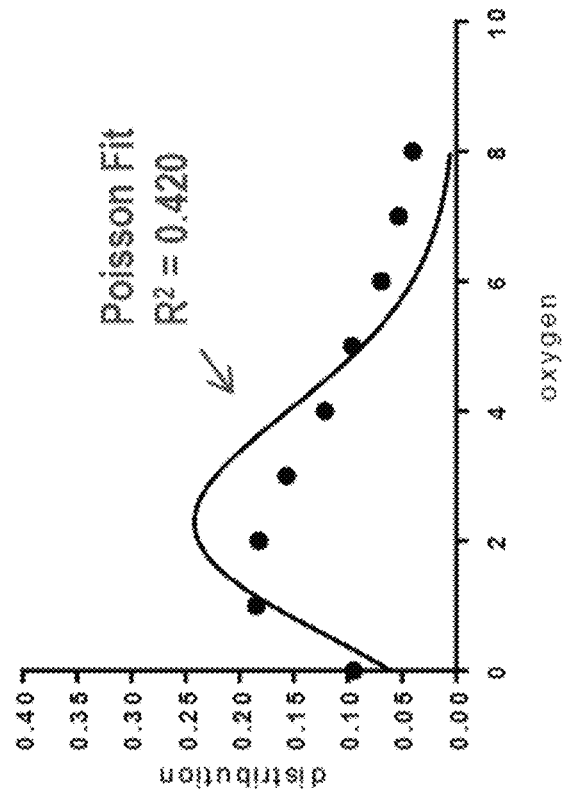

Results:

Table 2 shows the experimental parameters for FIGS. 6A and 6B. As seen in FIGS. 6A and 6B, position and laser power affect the labeling efficiency of lysozyme protein. The oxidized species in the sample that was analyzed using the parameters of FIG. 6B, including a closer focusing position and a laser power of 122 mJ, show a good fit of the +0, +16, +32 . . . state product distribution to a Poisson distribution. This is indicative of increased labeling efficiency.

TABLE 2

Experimental parameters

| Focusing Position | Position 1 (further, more focusing) | Position 2 (closer, less focusing) |
| --- | --- | --- |
| Protein Concentration | 0.2 mg/mL | 0.2 mg/mL |
| Laser Power | 168 mJ | 122 mJ |
| Scavenger | 350 µM His | 350 µM His |

As demonstrated by the Poisson distribution date in FIGS. 7A-7F and 8A-8D, laser power and scavenger concentration affect the labeling efficiency of protein at a much greater level than protein concentration.

Figure 9A:
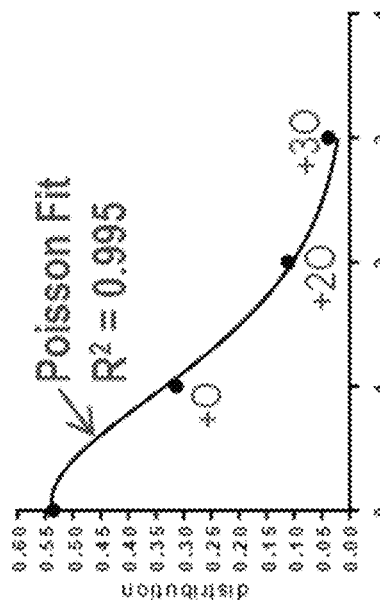
FIGS. 9A-9B are scatter plots showing Poisson fitting of oxidized species for mAb1 (FIG. 9A) or deglycosylated mAb1 (FIG. 9B).
Figure 9B:
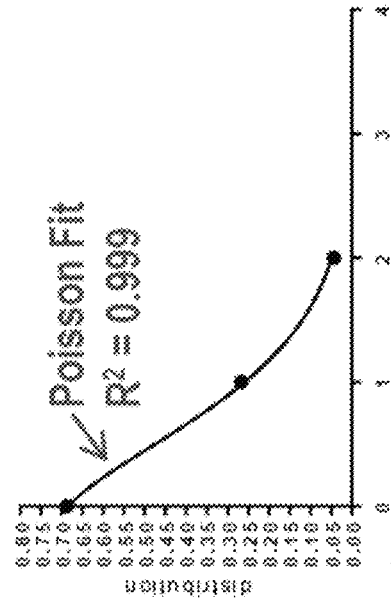

Deglycosylated mAb1 without buffer exchange shows decreased labeling extent (FIG. 9B) compared to mAb1 subjected to buffer exchange (FIG. 9A). This suggests that quenchers can interfere with protein oxidative labeling.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references mentioned throughout this disclosure are incorporated herein by reference in their entirety.

We claim:

1. A method for identifying noncovalent interaction sites or dimerization interfaces in a protein drug product, comprising:
    employing limited enzymatic digestion of a protein drug product under native conditions to form a protein drug dimer sample mixture comprising monomers and noncovalently linked dimers;
    introducing detectable modifications into the dimers and monomers of the protein drug dimer sample mixture to produce modified dimers and modified monomers, wherein the detectable modifications are introduced by fast photochemical oxidation of proteins;
    separating the modified dimers and modified monomers using native size exclusion chromatography into modified dimer and modified monomer fractions;
    digesting the modified dimer and modified monomer fractions to form peptide samples;
    separating the peptide samples using liquid chromatography/mass spectrometry (LC-MS) to obtain mass spectrometry data of the peptide samples;
    determining modification sites in each peptide in the peptide samples using the mass spectrometry data of the peptides compared to known mass data of the protein drug product by calculating the mass of each peptide and modified peptide of such protein drug product.

2. The method of claim 1, wherein native limited digestion conditions retain disulfide bonds between polypeptides and noncovalent interactions between dimers.

3. The method of claim 1, wherein the protein drug product comprises an antibody or an antigen binding fragment thereof, a recombinant protein, a fusion protein, or a combination thereof.

4. The method of claim 1, wherein the protein drug product is an antibody, and the dimers in the mixture consist essentially of two interacting F(ab') or F(ab) fragments.

5. The method of claim 1, wherein the protein drug product is an antibody, and the monomers in the mixture consist essentially of F(ab) fragments and Fc fragments.

6. The method of claim 1, wherein the modification is an amino acid side chain modification.

7. The method of claim 3, wherein the antibody is a monoclonal antibody, a bispecific antibody, or an antigen binding fragment thereof.

8. The method of claim 1, wherein the native size exclusion chromatography is performed using a mobile phase comprising ammonium acetate and ammonium bicarbonate.

9. The method of claim 1, wherein the digested protein sample is separated with reverse phase liquid chromatography.

10. The method of claim 1, wherein the modification is selected from the group consisting of oxidation, dioxidation, trioxidation, kynurenine, dithiomethyl, decarboxylation, hydroxykynurenine, and combinations thereof.

11. The method of claim 1, wherein the protein drug product is digested with an enzyme.

12. The method of claim 11, wherein the enzyme is selected from the group consisting of papain, ficain, endoprotease Lys-C and IdeS or a modified form thereof.

13. The method of claim 1, wherein the modified dimer and modified monomer fractions are digested by an enzyme that breaks covalent chemical bonds linking two consecutive amino acid residues to form peptides.

14. The method of claim 1, wherein the protein drug product sample is from a fed-batch culture, a purification process step, or a formulated drug substance.

15. A method of producing an antibody, comprising:
    culturing cells producing the antibody in a cell culture under suitable conditions to produce the antibody;
    purifying the antibody under suitable conditions to extract the antibody;
    admixing the antibody with excipients under suitable conditions to stabilize the antibody;
    obtaining a sample of the antibody i) from the cell culture, ii) following purification of the antibody from the cell culture, or iii) following the addition of excipients to the purified antibody;
    characterizing dimerization interfaces or noncovalent interaction sites of the antibody according to the method of claim 1, and
    modifying one or more cell culture, purification or excipient conditions to reduce the amount of dimerization or noncovalent interaction of the antibody.

16. The method of claim 15, wherein the one or more conditions that are changed to reduce the amount of dimerization or noncovalent interaction are selected from the group consisting of pH, cell density, amino acid concentration, osmolality, growth factor concentration, agitation, dissolved oxygen, metal ions, gas partial pressure, affinity matrix, chromatography resin, buffer, surfactant, stabilizer, or combinations thereof.

17. The method of claim 15 wherein the cells are selected from the group consisting of bacterial cells, yeast cells, Chinese Hamster Ovary (CHO) cells (e.g. CHO K1, DXB-11 CHO, Veggie-CHO), COS cells (e.g. COS-7), retinal cells, Vero cells, CV1 cells, kidney cells (e.g. HEK293, 293 EBNA, MSR 293, MDCK, HaK, BHK21), HeLa cells, HepG2 cells, W138 cells, MRC 5 cells, Colo25 cells, HB 8065 cells, HL-60 cells, lymphocyte cells, e.g. autologous T cells, Jurkat (T lymphocytes) or Daudi (B lymphocytes), A431 (epidermal) cells, U937 cells, 3T3 cells, L cells, C127 cells, SP2/0 cells, NS-0 cells, MMT cells, stem cells, tumor cells, and a cell line derived from any of the aforementioned cells.

18. The method of claim 15, wherein the cells are hybridoma cells or quadroma cells.

19. The antibody produced by the method of claim 15.

20. A method of making a modified antibody, comprising:
characterizing dimerization interfaces or noncovalent interaction sites in the antibody using the method of claim 1, and
modifying amino acids in the dimerization interfaces or noncovalent interaction sites to reduce dimerization or noncovalent interaction of the antibody.

21. The modified antibody of claim 20.

22. The antibody of claim 20, wherein the antibody is a monoclonal antibody or an antigen binding fragment thereof.

\* \* \* \* \*